(12) United States Patent
Carey et al.

(10) Patent No.: US 7,829,292 B2
(45) Date of Patent: Nov. 9, 2010

(54) COMPOSITIONS AND METHODS FOR DIAGNOSING, PREDICTING THERAPEUTIC RESPONSE OF, AND MONITORING AUTOIMMUNE DISEASE

(75) Inventors: Thomas E. Carey, Dexter, MI (US); Thankam S. Nair, Ann Arbor, MI (US); Jennifer Gray-Beckman, Falls Church, VA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 539 days.

(21) Appl. No.: 11/406,156

(22) Filed: Apr. 18, 2006

(65) Prior Publication Data

US 2007/0015209 A1 Jan. 18, 2007

Related U.S. Application Data

(63) Continuation-in-part of application No. 10/139,496, filed on May 6, 2002, now abandoned.

(60) Provisional application No. 60/672,453, filed on Apr. 18, 2005.

(51) Int. Cl.
*G01N 33/53* (2006.01)
(52) U.S. Cl. ..................................... 435/7.1
(58) Field of Classification Search ........................ None
See application file for complete search history.

(56) References Cited

U.S. PATENT DOCUMENTS

| 4,208,479 A | 6/1980 | Zuk et al. |
| 5,422,282 A | 6/1995 | Harris |
| 2003/0082646 A1* | 5/2003 | Carey et al. ................. 435/7.21 |

OTHER PUBLICATIONS

Stites, D.P., et al. Basic and Clinical Immunology. 1987;pp. 128-132.*
Disher, M.J., et al. Annals NY Acad Sci. 1997;830:253-265.*
Harris JP, Fan JT, Keithley EM., Am J Otolaryngol 11:304-308, 1990.
Yamanobe S, Harris JP., Laryngoscope 103:319-325, 1993.
Database EMBL [Online] Feb. 16, 2000, "Homo sapiens CTL2 gene" XP002377229 retrieved from EBI accession No. EM_PRO:AJ245621 Database accession No. AJ245621.
Nair et al., Hear Res 129:50-60, 1999.
Zavod et al., "Frequency of cochlear enhancement on magnetic resonance imaging in patients with autoimmune sensorineural hearing loss." 2000, Archives of Otolaryngology—Head & Neck Surgery, vol. 126, pp. 969-971.
O'Regan et al., Proc Natl Acad Sci USA 97:1835-1840, 2000.
Ptok et al., Hear Res 66:245-252, 1993.
Fransen et al., 1999, Hum Mol Gen. vol. 8, No. 8, pp. 1425-1429.
Robertson et al., 1998, Nat. Gen. vol. 20:299-303.
Boulassel et al., 2001, Otol Neurol, vol. 22:614-618.
Manolis et al., 1996, Hum. Mol. Gen. vol. 5, No. 7, pp. 1047-1050.
Roberton et al., 1997, Genomics 46, 345-354.
Heller et al., 1998, Proc. Natl. Acad. Sci. USA, vol. 95, pp. 11400-11405, Neurobiology.
Yvette et al., 1999, Hum. Mol. Gen., vol. 8, No. 2, pp. 361-366.
Alberts et al., Molecular Biology of the Cell, 2nd Edition, 1989, pp. 163-196, 258-271.
McCabe B.F. "Autoimmune Sensorineural Hearing Loss," Ann Otol, 88:585-859, 1979.
Harris and Ryan "Immunobiology of the Inner Ear", Am J Otolaryngol, 5:418-425, 1984.
Cruz et al. "Autoimmune Sensorineural Hearing Loss: A Preliminary Experimental Study", Am J Otol, 11:342-346, 1990.
Harris "Immunology of the Inner Ear: Response of the Inner Ear to Antigen Challenge", Otolaryngol Head Neck Surg ,91: 18-23, 1983.
Arnold et al. "Evidence of Serum Antibodies Against Inner Ear Tissues in the Blood of Patients with Certain Sensorineural Hearing Disorders", Acta Otolaryngol99:437-444, 1985.
Moscicki et al. "Serum Antibody to Inner Ear Proteins in Patients with Progressive Hearing Loss: Correlation with Disease Activity and Response to Corticosteroid Treatment", JAMA 272:611-616, 1994.
Sismanis et al. "Methotrexate Management of Immune-Mediated Cochleovestibular Disorders", Otolaryngol Head Neck Surg, 116:146-152, 1997.
Rauch et al. "Serum Antibodies Against Heat Shock Proteins in Meniere's Disease", Am J Otology, 16:648-652, 1995.
McCabe BF "Autoimmune Inner Ear Disease: Results of Therapy", In: Bearing of Basic Research on Clinical Otolaryngolog,. Adv Otorhinolaryngol, Pfaltz CR, Arnold W, Kleinsasser 0 (eds), Karger Publishing, Basel, Switzerland, vol. 46, pp. 78-81, 1991.
Hughes et al. "Practical Versus Theoretical Management of Autoimmune Inner Ear Disease", Laryngoscope, 94:758-767, 1984.
Kanzaki J and O-Uchi T "Circulating Immune Complexes in Steroid-Responsive Sensorineural Hearing Loss and the Long-Term Observation", Acta Otolaryngol (suppl), 393:77-84, 1983.
Hughes et al. "Clinical Diagnosis of Immune Inner-Ear Disease", Laryngoscope, 98:251-253, 1988.
Veldman et al. "Autoimmunity and Inner Ear Disorders: An Immune-Complex Mediated Sensorineural Hearing Loss", Laryngoscope, 94:501-507, 1984.
Mattox and Lyles "Idiopathic Sudden Sensorineural Hearing Loss", Am J Otol, 10:242-247, 1989;Mattox and Lyles "Idiopathic Sudden Sensorineural Hearing Loss", Am J Otol, 10:242-247, 1989.
Mattox and Simmons "Natural History of Sudden Sensorineural Hearing Loss", Ann Otol Rhinol Laryngol, 86:463-480, 1977.
Billings et al. "Evidence Linking the 68 Kilodalton Antigen Identified in Progressive Sensorial Hearing Loss Patient Sera with Heat Shock Protein 70", Ann Otol Rhinol Laryngol, 104:181-188, 1995.
Harris and Sharp "Inner Ear Antibodies in Patients with Rapidly Progressive Sensorineural Hearing Loss", Laryngoscope, 100:516-524, 1990.

(Continued)

*Primary Examiner*—G. R Ewoldt
(74) *Attorney, Agent, or Firm*—Casimir Jones S.C.

(57) ABSTRACT

The present invention provides methods of diagnosing the presence of an autoimmune disease in a patient, methods of predicting the response of an autoimmune diseased patient to therapeutic treatment, and methods of monitoring an autoimmune patient's response to therapy. In particular, these methods comprise the use of a glycoprotein from the inner-ear organ of Corti reactive with a KHRI-3 monoclonal antibody.

6 Claims, 1 Drawing Sheet

OTHER PUBLICATIONS

Shin et al. "Comparison of Anti-Heat Shock Protein (Anti-hsp70) and Anti-68-kDa Inner Ear Protein in the Sera of Patients with Meniere's Disease"; Laryngoscope; 107:222-227, 1997.
Yoo et al. "Factors Influencing Collagen-Induced Autoimmune Ear Disease", Am. J Otolaryngol, 6:209-216, 1983.
Harris "Experimental Autoimmune Sensorineural Hearing Loss", Laryngoscope, 97:63-76, 1987.
Orozco et al. "Experimental Model of Immune-Mediated Hearing Loss Using Cross-Species Immunization", Laryngoscope, 100:941-947, 1990.
Kusakari et al. "MLRIMP-q:,r/Ipr Mouse as a Model of Immune-Induced Sensorineural Hearing Loss", Ann. Olol. Rhinol. Laryngol., 101:82-86, 1992.
Tago et al. "Cochlear and Renal Pathology in the Autoimmune Strain Mouse", Ann. 0101. Rhinol. Laryngol. 157 (Suppl.):87-91, 1992.
Wong et al. "Cochlear IgG in the C3H/Ipr Autoimmune Mouse Strain", Hear. Res., 59:93-100, 1992.
Sone et al. "A Substrain of NZB Mouse as an Animal Model of Autoimmune Inner Ear," Hear. Res., 83: 26-36, 1994.
Harris and Ryan "Fundamental Immune Mechanisms of the Brain and Inner Ear", Otolaryngol. Head Neck Surg., 112:639-653, 1995.
Gottschlich et al. "Assessment of Serum Antibodies in Patients with Rapidly Progressive Sensorineural Hearing Loss and Meniere's Disease", Laryngoscope, 105:1347-1352, 1995.
Cao et al. "Detection of Inner Ear Disease Autoantibodies by Immunoblotting", Mol. Cell Biochem., 146:157-163, 1995.
Nair et al. "Monoclonal Antibody Induced Hearing Loss", Hear. Res., 83:101-113, 1995.
Cao et al. "Guinea Pig Inner Ear Antigens: Extraction and Application to the Study of Human Autoimmune Inner Ear Disease", Laryngoscope, 106:207-212, 1996.
Zajic et al. "Monoclonal Antibodies to Inner Ear Antigens: 1. Antigens Expressed by Supporting Cells in Guinea Pig Cochlea", Hear. Res., 52:59-72, 1991.
Ptok et al. "Monoclonal Antibodies to Inner Ear Antigens: II. Antigens Expressed in Sensory Cell Stereocilia", Hear. Res., 57:79-90, 1991.
Nair et al. "In vivo Binding and Hearing Loss After Intracochlear Infusion of KHRI-3 Antibody", Hear. Res., 107:93-101, 1997.
Hughes et al. "Laboratory Diagnosis of Immune Inner Ear Disease", Am. J. Otolog., 15:198-202, 1994.
Bloch et al. "Serum Antibodies to Heat Shock Protein 70 in Sensorineural Hearing Loss", Arch Otoloaryngol Head Surg, 121:1167-1171, 1996.
Figuerdo et al. "Increased Serum Levels of IgA Antibodies to hsp70 Protein in Patients with Diabetes Mellitus: Their Relationship with Vascular Complications", Clin Immunol Immunopathol, 79:252-255, 1995.
Shingai et al. "Autoantibody Against 70 kD Heat Shock Protein in Patients with Autoimmune Liver Diseases", J Hepatol, 23:382-390,1995.
Paggi et al. "Anti 70 kDa Heat Shock Protein Antibodies in Sera of Patients Affected by Autoimmune and Non-Autoimmune Thyroid Diseases"; Endocr Res; 21:555-567, 1995.
Anhalt et al. "Mechanisms of Immunologic Injury. Pemphigus and Pemphigoid.", Arch Dermatol., 119:711-714, 1983.
Wilkin "Receptor Autoimmunity in Endocrine Disorders", N Engl J Med, 323:1318-1324, 1990.
Amagai et al. "Autoantibodies Against the Amino-Terminal Cadherin-Like Binding Domain of Pemphigus Vulgaris Antigen are Pathogenic", J C/in Invest, 90:919-926, 1992.
Feldt-Rasmussen et al. "Anti-Thyroid Peroxidase Antibodies in Thyroid Disorders and Non-Thyroid Autoimmune Diseases", Autoimmunity, 9:245-254, 1991.
Mappouras et al. "Antibodies to Acetylcholinesterase Cross-Reacting with Thyroglobulin in Myasthenia Gravis and Graves's Disease", Clin Exp Immunol, 100:336-343, 1995.
Chiovato et al. "Antibodies Producing Complement-Mediated Thyroid Cytotoxicity in Patients with Atrophic or Goitrous Autoimmune Thyroiditis", J Clin Endocrinol Metab, 77:1700-1705, 1993.
Li et al."Catalytic Activity of Anti-Thyroglobulin Antibodies", J Immunol, 154:3328-3332, 1995.
Scheinin et al. "Islet Cell and Glutamic Acid Decarboxylase Antibodies and Heat-Shock Protein 65 Responses in Children with Newly Diagnosed Insulin-Dependent Diabetes Mellitus", Immunol Lell, 49:123-126, 1996.
Nair et al., "KHRI-3 antigen is distinct from heat shock protein 70," Association for Research in Otolaryngology~ Feb. 15-19, 1998.
Harris et al., "Immunologic mechanisms in disorders of the inner ear" 2nd edition Otolaryngology Head and neck Surgery, vol. IV: Ear and Cranial Base, 1993, pp. 2926-2942.
Gebbers JO, Altermatt HJ, Arnold W, Laissue JA Pfaltz CR, Methyodologic limits. HNO 35:487-487-491 (1987).
Soliman AM, Zanetti F., Adv Otol Rhinol-Laryngol 39:17, 1988.

* cited by examiner

FIGRUE 1
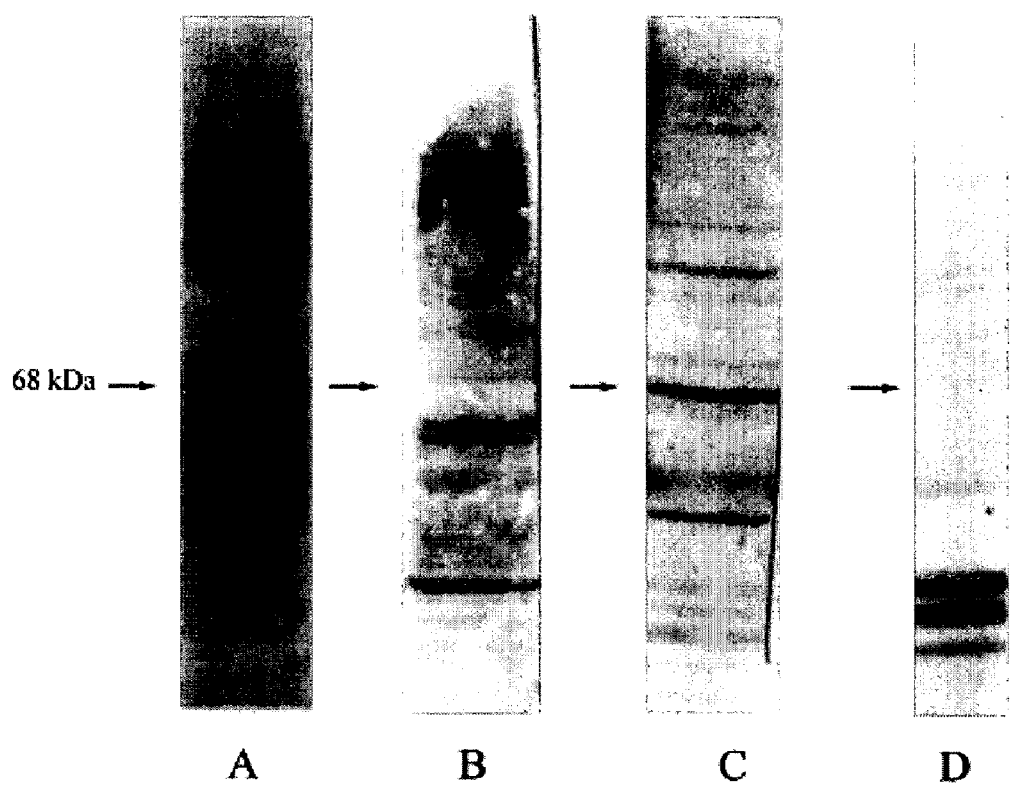
68 kDa →
A  B  C  D

COMPOSITIONS AND METHODS FOR DIAGNOSING, PREDICTING THERAPEUTIC RESPONSE OF, AND MONITORING AUTOIMMUNE DISEASE

This application is a continuation-in-part of co-pending U.S. patent application Ser. No. 10/139,496, filed May 6, 2002 and also claims priority to U.S. Provisional Patent Application No. 60/672,453, filed Apr. 18, 2005, each of which is hereby incorporated by reference in its entirety.

This invention was funded, in part, under NIH Grants 1 P30 AR048310, NIDCD P30 DC05188, P01 DC00078, NIDCD RO1 DC02272 and RO1 DC03686. The government may have certain rights in the invention.

FIELD OF THE INVENTION

The present invention provides methods of diagnosing the presence of an autoimmune disease in a patient, methods of predicting the response of an autoimmune diseased patient to therapeutic treatment, and methods of monitoring an autoimmune patient's response to therapy. In particular, these methods comprise the use of a glycoprotein from the inner-ear organ of Corti (IESCA) reactive with a KHRI-3 monoclonal antibody.

BACKGROUND OF THE INVENTION

Autoimmune diseases are thought to result from a breakdown in control of the immune system and its inherent tolerance to self antigens. There are several different autoimmune diseases and they affect millions of people worldwide. One or more tissues of the body is generally attacked by the immune system in autoimmune diseases. For example, in multiple sclerosis (MS), myasthenia gravis and autoimmune ureitis, the nervous system is attacked. In Crohn's disease and ulcerative colitis, the gastrointestinal system is attacked, and in psoriasis, pemphigus vulgaris and vitiligo, the skin is affected. Several autoimmune diseases attack multiple organs, for example, systemic lupus erythematosus (SLE), rheumatoid arthritis and scleroderma.

These diseases are characterized by the presence of a multitude of autoreactive antibodies that arise spontaneously. To date, high levels of circulating autoantibodies to DNA are the best evidence of these maladies.

Cross reactivity of antibodies raised in the normal way to a foreign antigen is also a potential source of autoimmune disease, for example, antibodies against streptococcal M protein can cross react with human heart muscle.

Unexplained or idiopathic sensorineural hearing loss (SNHL) is troubling to physicians and patients alike because the etiology is unknown and there are few effective treatments. Autoimmunity is suspected to be a cause of some cases of sudden onset, rapidly progressive or fluctuating hearing loss, particularly when bilateral involvement occurs. Autoimmune sensorineural hearing loss (AISNHL) in humans has been suspected in systemic autoimmune diseases, and there are indications that inner ear organ-specific autoimmunity is involved in rapidly progressive hearing loss (Harris J P (1993 In: 2nd edition, Otolaryngology Head and Neck Surgery, Vol IV: Ear and Cranial Base (Cummings C W, Krause C J, Schuller D E, Fredrickson J M, Harker L A (eds), Mosby Yearbook, St. Louis, Mo.) pp. 2926-2942; McCabe B F (1979) Ann. Otol. 88:585-859; McCabe B F (1991) In: Bearing Of Basic Research On Clinical Otolaryngology, Adv. Otorhinolaryngol (Pfaltz C R, Arnold W, Kleinsasser O (eds), Karger Publishing, Basel, Switzerland, Vol. 46) pp. 78-81; Hughes et al (1988) Laryngoscope 98:251-253; Harris and Ryan (1984) Am. J. Otolaryngol. 5:418-425; Cruz et al. (1990) Am. J. Otol. 11:342-346; Harris (1983) Otolaryngol Head Neck Surg. 91:17; Arnold et al. (1985) Acta Otolaryngol 99:437; Harris and Sharp (1990) Laryngoscope 100:516-524; Moscicki et al. (1994) JAMA 272:611-616; Sismanis et al. (1997) Otolaryngol Head Neck Surg. 116:146-152).

Given the high frequency of idiopathic SNHL, the ability to accurately diagnose AISNHL would be of value since this is one of the few potentially treatable causes of SNHL. However, since treatment of autoimmune disease involves toxic drugs such as corticosteroids, cyclophosphamide, methotrexate and cyclosporin A, all of which have significant side effects, most physicians are reluctant to use these agents without a clear indication (Sismanis et al. (1997) Otolaryngol Head Neck Surg. 116:146-152). Treatment of suspected autoimmune hearing loss is complicated, because without treatment there is a high frequency of spontaneous remission, but in cases that don't regress, the hearing loss may become worse and permanent. Immune-mediated hearing loss also may include 30-50% of Meniere's disease (episodic vertigo and fluctuating progressive hearing loss) patients (Rauch et al (1995) Am. J. Otology 16:648-652; Shin et al. (1997) Laryngoscope 107:222-227).

Early approaches to detecting AISNHL employed cellular assays of immune reactivity, such as lymphocyte transformation and lymphocyte migration inhibition assays using crude inner ear antigens (McCabe B F (1991) In: Bearing Of Basic Research On Clinical Otolaryngology, Adv. Otorhinolaryngol (Pfaltz C R, Arnold W, Kleinsasser O (eds), Karger Publishing, Basel, Switzerland) Vol. 46, pp. 78-81; Hughes et al (1984) Laryngoscope 94:758-767). Unfortunately, these assays did not correlate well with response to therapy (Hughes et al. (1984) Laryngoscope 94:758-767; Kanzaki J and O-Uchi T (1983) Acta. Otolaryngol. (suppl.), 393:77-84; Hughes et al. (1988) Laryngoscope 98:251-253; Veldman et al (1984) Laryngoscope 94:501-507). The poor predictability has been explained by a lack of sensitivity and specificity of these assays for identifying organ-specific autoimmune reactivity (Mattox and Lyles (1989) Am. J. Otol. 10:242-247; Mattox and Simmons (1977) Ann. Otol. Rhinol. Laryngol. 86:463-480).

Autoimmune diseases typically cause a great deal of discomfort and pain in the patient. Clearly, there is a need for a rapid, distinctive and accurate assay that is diagnostic for autoimmune diseases (e.g., rheumatoid arthritis or AISNHL). This rapid diagnosis would aid the clinician in properly prescribing an effective therapeutic regimen to alleviate the pain and symptoms associated with the disease. Furthermore, it would be highly beneficial for clinicians to determine apriori which patients are likely to respond to therapeutic treatment (e.g., immunosuppressive therapy), thereby avoiding the risks associated with such therapy in the population of patients unlikely to respond.

SUMMARY OF THE INVENTION

The present invention provides methods of diagnosing the presence of an autoimmune disease in a patient, methods of predicting the response of an autoimmune diseased patient to therapeutic treatment, and methods of monitoring an autoimmune patient's response to therapy. In particular, these methods comprise the use of a glycoprotein from the inner-ear organ of Corti (IESCA) reactive with a KHRI-3 monoclonal antibody.

Accordingly, in some embodiments, the present invention provides a method for predicting the response of an autoimmune diseased patient to therapeutic treatment, comprising providing a glycoprotein from the inner-ear organ of Corti reactive with a KHRI-3 monoclonal antibody and serum from a patient suspected of having an autoimmune disease; contacting the glycoprotein with the serum under conditions sufficient to effect binding of the antibody to the glycoprotein; detecting binding of an antibody in the serum to the glycoprotein; and correlating the presence or absence of the binding of an antibody in the serum to the glycoprotein to the response of the autoimmune patient to the therapeutic treatment. In some embodiments, the presence of antibody binding correlates with a subject that is likely to respond to therapeutic treatment. In some embodiments, the therapeutic treatment comprises immunosuppressive therapy. In some embodiments, the immunosuppressive therapy comprises treatment with steroids or steroid analogues. In some embodiments, the autoimmune disease is a systemic autoimmune disease. The present invention is not limited by the type of autoimmune disease detected. Indeed, a variety of autoimmune diseases can be detected by the compositions and methods of the present invention including, but not limited to, systemic autoimmune diseases such as rheumatoid arthritis, multiple sclerosis, juvenile-onset diabetes, systemic lupus erythematosus (SLE), Cogan's syndrome, unclassified systemic autoimmune disease, Raynaud's syndrome, Wegener's granulomatosis, autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, or autoimmune thrombocytopenic purpura. In a preferred embodiment, the autoimmune disease is autoimmune sensorineural hearing loss (AISNHL). In some embodiments, the presence of binding of an antibody in the serum to the glycoprotein correlates with a subject that displays a positive response to the therapeutic treatment. In some embodiments, the presence of antibody binding to the glycoprotein permits early diagnosis of autoimmune disease. In some embodiments, early diagnosis of autoimmune disease permits use of treatments for the subject that would not be used at a later stage of disease.

The present invention also provides a method for identifying the presence of an autoimmune disease in a subject, comprising providing a glycoprotein from the inner-ear organ of Corti reactive with a KHRI-3 monoclonal antibody and serum from the subject; contacting the glycoprotein with the serum under conditions sufficient to effect binding of glycoprotein-specific antibodies, if present in the serum, to the glycoprotein; detecting binding of the antibodies to the glycoprotein; and correlating the presence or absence of binding to the presence or absence of an autoimmune disease in the patient. In some embodiments, the subject is suspected of having an autoimmune disease. In some embodiments, detection of binding of the antibodies to the glycoprotein is indicative of an autoimmune disease in the subject. In some embodiments, the autoimmune disease is autoimmune sensorineural hearing loss. The present invention is not limited by the type of autoimmune disease identified. Indeed, a variety of autoimmune diseases can be identified using the compositions and methods of the present invention including, but not limited to, rheumatoid arthritis, multiple sclerosis, juvenile-onset diabetes, systemic lupus erythematosus, Cogan's syndrome, unclassified systemic autoimmune disease, Raynaud's syndrome, Wegener's granulomatosis, autoimmune uveoretinitis, autoimmune vasculitis, bullous pemphigus, myasthenia gravis, autoimmune thyroiditis, Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura. In some embodiments, detection of binding of the antibodies to the glycoprotein is indicative of a subject more likely to respond to therapeutic treatment compared to a subject from whom binding of the antibodies to the glycoprotein is not detected. In some embodiments, therapeutic treatment comprises immunosuppressive therapy. In some embodiments, the immunosuppressive therapy comprises treatment with steroids. In some embodiments, immunofluorescence is used for the detecting. In some embodiments, the detecting comprises Western blotting. In some embodiments, the glycoprotein from the inner-ear organ of Corti reactive with a KHRI-3 monoclonal antibody is CTL2. In some embodiments, the CTL2 is immunopurified CTL2. In some embodiments, the CTL2 is recombinant CTL2.

The present invention also provides a kit for assaying for the presence of an antibody associated with autoimmune sensorineural hearing loss in a patient, wherein the composition comprises an inner ear supporting cell antigen (IESCA), a glycoprotein from the inner-ear organ of Corti reactive with a KHRI-3 monoclonal antibody. The present invention is not limited by the type of IESCA protein utilized. Indeed, a variety of IESCA proteins are contemplated to be useful in the present invention including, but not limited to, immunopurified IESCA, recombinant IESCA, chemically synthesized IESCA, or analogues or variants thereof. In some preferred embodiments, IESCA is CTL2.

The present invention also provides a method for monitoring an autoimmune patient's response to therapy, comprising providing a glycoprotein from the inner-ear organ of Corti reactive with a KHRI-3 monoclonal antibody and serum from a patient suspected of having an autoimmune disease; contacting the glycoprotein with the serum under conditions sufficient to effect binding of the antibody to the glycoprotein; detecting binding of an antibody in the serum to the glycoprotein; and correlating the presence or absence of the binding of an antibody in the serum to the glycoprotein to the response of the autoimmune patient to the therapeutic treatment.

In some embodiments, the therapy comprises immunosuppressive therapy. The present invention is not limited by the type of immunosuppressive therapy administered. Indeed, a variety of immunosuppressive therapies may be administered including, but not limited to, steroids (e.g., corticosteroids) and steroid analogues. In preferred embodiments, a decrease in detectable levels of antibody (e.g., compared to levels detected without therapy) to a glycoprotein from the inner-ear organ of Corti reactive with a KHRI-3 monoclonal antibody correlates with a favorable response to immunosuppressive therapy.

The present invention also provides a method of treating an autoimmune disease comprising administering to a patient suspected of having the autoimmune disease a composition comprising a glycoprotein from the inner-ear organ of Corti reactive with a KHRI-3 monoclonal antibody or other agents (e.g., protein fragments or antibodies) that bind to KHRI-3 monoclonal antibodies.

DESCRIPTION OF THE DRAWINGS

FIG. 1 depicts the Western blot of inner ear proteins stained with sera. Panel A UMHL-80, panel B UMHL-82, panel C UMHL-48, and panel D UMHL-54. The arrows show the migration position of proteins with a relative molecular mass (Mr) of 68 kDa.

DEFINITIONS

To facilitate an understanding of the present invention, a number of terms and phrases as used herein are defined below:

The term "sensorineural hearing loss (SNHL)" refers to a disease characterized by progressive unilateral or bilateral deafness resulting from damage to sensory cells or nerves or other components of the inner ear necessary for processing sounds, that, in its incipient stages, may fluctuate or become sudden and profound.

The term "autoimmune sensorineural hearing loss (AIS-NHL)" refers to sensorineural hearing loss whose etiology includes the generation of autoantibodies directed against inner ear antigenic epitopes.

The term "autoimmune/autoimmunity" refers to a condition where antibodies recognize self-antigens as foreign and thereby initiate an immune response to cells, tissues or organs often causing the establishment and continuation of a disease state.

The terms "auto-antibody" or "autoimmune antibody" refer to an antibody which recognizes a self-antigen as foreign.

As used herein, the term "autoimmune disease" means a set of sustained organ-specific or systemic clinical symptoms and signs associated with altered immune homeostasis that is manifested by qualitative and/or quantitative defects of expressed autoimmune repertoires. Autoimmune diseases are characterized by antibody or cytotoxic immune responses to epitopes on self antigens found in the diseased individual. The immune system of the individual then activates an inflammatory cascade aimed at cells and tissues presenting those specific self antigens. The destruction of the antigen, tissue, cell type, or organ attacked by the individual's own immune system gives rise to the symptoms of the disease. Clinically significant autoimmune diseases include, for example, rheumatoid arthritis, multiple sclerosis, juvenile-onset diabetes, systemic lupus erythematosus (SLE), Cogan's syndrome, unclassified systemic autoimmune disease, Raynaud's syndrome, Wegener's granulomatosis, autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, or autoimmune thrombocytopenic purpura.

As used herein, the term "subject suspected of having autoimmune disease" refers to a subject that presents one or more symptoms indicative of an autoimmune disease (e.g., hearing loss, hives or joint pain) or is being screened for an autoimmune disease (e.g., during a routine physical). A subject suspected of having an autoimmune disease may also have one or more risk factors. A subject suspected of having an autoimmune disease has generally not been tested for autoimmune disease. However, a "subject suspected of having autoimmune disease" encompasses an individual who has received an initial diagnosis but for whom the severity of the autoimmune disease is not known. The term further includes people who once had autoimmune or chronic inflammatory disease but whose symptoms have ameliorated. In contrast, a "subject identified as having an autoimmune disease" refers to a subject that have been diagnosed by a physician (e.g., using methods well known in the art) as having autoimmune disease.

As used herein, the term "subject at risk for autoimmune disease" refers to a subject with one or more risk factors for developing an autoimmune disease. Risk factors include, but are not limited to, gender, age, genetic predisposition, environmental exposure, previous incidents of autoimmune or chronic inflammatory disease, preexisting non-autoimmune diseases, and lifestyle.

The terms "antibody" or "immunoglobulin" refer to proteins that bind a specific antigen. Immunoglobulins include, but are not limited to, polyclonal, monoclonal, chimeric, and humanized antibodies, Fab Fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies. Antibodies may be produced by any of the known methodologies (See, e.g., Current Protocols in Immunology (1998) John Wiley and Sons, Inc., N.Y.).

The term "epitope" refers to the portion of an antigen that makes contact with a particular antibody or immunoglobulin.

The term "antigen" refers to a protein, glycoprotein, lipoprotein, lipid or other substance that is reactive with an antibody specific for a portion of the molecule. The term "inner ear antigens" refers to antigens from the inner ear that are reactive with autoantibodies associated with AISNHL.

The term "Inner-Ear Supporting Cells Antigen (IESCA)" refers to molecules (proteins, glycoproteins, lipoproteins or other molecules reactive with antibodies), or portions thereof, that are localized with high specificity to the supporting cells of the inner ear and are reactive with KHRI-3 MAb. In the context of this patent application the following shall generally apply: Expression of these molecules in other tissues does not exclude them from being IESCA. Likewise, absence of these molecules from the inner ear supporting cells in certain circumstances (such as disease) does not exclude them from being IESCA. Furthermore, variation in molecular weight of IESCA from that disclosed here, so long as they are reactive with KHRI-3 MAb, does not exclude them from being IESCA.

The term "inner ear organ of Corti" refers to the structure within which specialized sensory cells, or hair cells, are arranged in the inner ear or cochlea; these cells are arranged in order from the high frequency region in the base of the cochlea to the low frequency in the apex. The hair cells are so named because they have stereocilia or long stiff projections from their upper surface. Sounds are transmitted from the eardrum to the inner ear by small bones called ossicles. These bones vibrate against a membrane in the cochlea transmitting the energy to the fluid inside. The fluid moves the organ of Corti stimulating hair cells at the appropriate frequency. The stimulated hair cells then stimulate nerves that send the information to the brain for processing. If hair cells are damaged or lost, then hearing is affected for the frequencies encoded by those sensory cells.

The term "anti-IESCA antibody" refers to an antibody that specifically binds to IESCA.

The term "KHRI-3" refers to a mouse monoclonal antibody which is specific to IESCA.

The term "glycoprotein" refers to a protein which has been post-translationally modified by glycosylation, or the addition of carbohydrate moieties to the protein.

The term "CTL-2" refers to a choline-transport-like protein 2, as for example identified by O'Regan (O'Regan, S. et al. (2000) Proc. Natl. Acad. Sci. U.S.A. 97 (4), 1835-1840). An exemplary amino sequence of human CTL2 is SEQ ID NO:2 of U.S. patent application Ser. No. 10/139,496, herein incorporated by reference in its entirety for all purposes.

As used herein, the term "glycoprotein-specific antibodies," when used in reference to detection of such antibodies in an assay of the present invention, refer to antibodies that bind to a glycoprotein from the inner-ear organ of Corti reactive with a KHRI-3 monoclonal antibody. Thus, in some embodiments, "glycoprotein-specific antibodies" bind to a IESCA (e.g., CTL2).

The terms "immunoprecipitate," "immunopurify," and "affinity purify," and grammatical variations such as verbs and adjectives, refer to the use of an antibody to separate its antigen or a portion thereof from a mixture of other molecules.

The term "staining" refers to as any number of processes known to those in the field that are used to better visualize, distinguish or identify a specific component(s) and/or feature(s) of a cell or cells.

The term "immunofluorescence" refers to a staining technique used to identify, mark, label, visualize or make readily apparent by procedures known to those practiced in the art, where a ligand (usually an antibody) is bound to a receptor (usually an antigen) and such ligand, if an antibody, is conjugated to a fluorescent molecule, or the ligand is then bound by an antibody specific for the ligand, and said antibody is conjugated to a fluorescent molecule, where said fluorescent molecule can be visualized with the appropriate instrument (e.g., a fluorescent microscope).

The term "morphology" refers to the visual appearance of a cell or organism when viewed, for example, with the eye, a light microscope, a confocal microscope or an electron microscope, as appropriate.

The term "patient" or "subject" refers to a human or other animal, such as a guinea pig or mouse and the like, capable of having an autoimmune disease (e.g., AISNHL), either naturally occurring or induced. The terms "patient" or "subject," thus refer to an individual to be diagnosed, treated (e.g., administered an immunosuppressive therapy) or monitored using the compositions and methods of the present invention. Generally, the terms patient and subject are used interchangeably, unless indicated otherwise herein.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "nascent" when used in reference to a protein refers to a newly synthesized protein, which has not been subject to post-translational modifications, which includes but is not limited to glycosylation and polypeptide shortening. The term "mature" when used in reference to a protein refers to a protein which has been subject to post-translational processing and/or which is in a cellular location (such as within a membrane or a multi-molecular complex) from which it can perform a particular function which it could not if it were not in the location.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include the transmembrane domains, and the glycosylation sites.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

In particular, the term "CTL2 gene" refers to a full-length CTL2 nucleotide sequence. However, it is also intended that the term encompass fragments of the CTL2 sequence, as well as other domains with the full-length CTL2 nucleotide sequence. Furthermore, the terms "CTL2 nucleotide sequence" or "CTL2 polynucleotide sequence" encompasses DNA, genomic DNA, cDNA, and RNA (e.g., mRNA) sequences.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise gene sequences that comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a fill-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.* 2: 482 (1981)) by the homology alignment algorithm of Needleman and Wunsch (Needleman and Wunsch, *J. Mol. Biol.* 48:443 (1970)), by the search for similarity method of Pearson and Lipman (Pearson and Lipman, *Proc. Natl. Acad. Sci.* (*U.S.A.*) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less. "Low stringency conditions" when used in reference to nucleic acid hybridization comprise conditions equivalent to binding or hybridization, for example, at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed. However, the present invention is not limited to the hybridization of probes of about 500 nucleotides in length. The present invention contemplates the use of probes between approximately 10 nucleotides up to several thousand (e.g., at least 5000) nucleotides in length. One skilled in the relevant art understands that stringency conditions may be altered for probes of other sizes (See e.g., Anderson and Young (1985) Quantitative Filter Hybridization, in Nucleic Acid Hybridization; and Sambrook et al. (1989) Molecular Cloning: A Laboratory Manual (Cold Spring Harbor Press, NY).

"Medium stringency conditions" when used in reference to nucleic acid hybridization comprise conditions equivalent to binding or hybridization, for example, at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization, for example, at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "allele" refers to different variations in a gene; the variations include but are not limited to variants and mutants, polymorphic loci and single nucleotide polymorphic loci, frameshift and splice mutations. An allele may occur naturally in a population, or it might arise during the lifetime of any particular individual of the population.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated.

A "splice mutation" refers to any mutation that affects gene expression by affecting correct RNA splicing. Splicing mutation may be due to mutations at intron-exon boundaries which alter splice sites.

The term "detection assay" refers to an assay for detecting the presence or absence of a wild-type or variant nucleic acid sequence (e.g., mutation or polymorphism) in a given allele of a particular gene (e.g., CTL2 gene), or for detecting the presence or absence of a particular protein (e.g., CTL2/IESCA) or the activity or effect of a particular protein (e.g., choline transport or a role in hearing) or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q β replicase, MDV-1 RNA is the specific template for the replicase (Kacian et al., Proc. Natl. Acad. Sci. USA, 69:3038 (1972)). Other nucleic acid will not be replicated by this amplification enzyme. Similarly, in the case of T7 RNA polymerase, this amplification enzyme has a stringent specificity for its own promoters (Chamberlin et al., Nature, 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue (e.g., inner ear) in the relative absence of expression of the same nucleotide sequence of interest in a different type of tissue (e.g., tongue). Tissue specificity of a promoter may be evaluated by, for example, operably linking a reporter gene to the promoter sequence to generate a reporter construct, introducing the reporter construct into the genome of an organism such that the reporter construct is integrated into every tissue of the resulting transgenic organism, and detecting the expression of the reporter gene (e.g., detecting mRNA, protein, or the activity of a protein encoded by the reporter gene) in different tissues of the transgenic organism. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York (1989) pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "transgenic" when used in reference to a host cell or an organism refers to a host cell or an organism that contains at least one heterologous or foreign gene in the host cell or in one or more of cells of the organism.

The term "host cell" refers to any cell capable of replicating and/or transcribing and/or translating a heterologous gene. Thus, a "host cell" refers to any eukaryotic or prokaryotic cell (e.g., bacterial cells such as $E.$ $coli$, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos. 6,074,859; 5,976, 796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31-9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of immunofluorescence and radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences encoding an immunopurified glycoprotein from the inner-ear organ of Corti reactive with KHRI-3 monoclonal antibody (e.g., CTL2/IESCA or fragments thereof) may be employed as hybridization probes. In this case, the CTL2 encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., increased or decreased presence of reporter protein, or binding of a protein (e.g., glycoprotein from the inner-ear organ of Corti reactive with a KHRI-3 monoclonal antibody) to antibodies (e.g., detected via immunofluorescence or Western blotting), increased in ion concentration, accumulation of a detectable chemical product, etc.). The term "favorable response" is used herein to refer to beneficial effects received by a patient after therapy (e.g., identified by decreased detection of binding of antibodies in the serum of a subject to IESCA after receiving treatment (e.g., immunosuppressive therapy); or, identification of a subject that is likely to respond favorably to treatment (e.g., immunosuppressive therapy) due to the presence of glycoprotein-specific antibodies in the subject's serum.

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DETAILED DESCRIPTION OF THE INVENTION

Sensorineural hearing loss (SNHL) is a common disorder affecting millions of people around the world. SNHL is the result of damage to either the sensory system within the inner ear or the nerves that carry information from the sensory system to the brain. The inner ear is a tiny organ comprised of specialized sensory cells. These specialized cells are called hair cells because they have stereocilia or long stiff projections from their upper surface. The hair cells are arranged in the inner ear or cochlea within the organ of Corti, in order from the high frequency region in the base of the cochlea to the low frequency region in the apex. Sounds are transmitted from the eardrum to the inner ear by small bones called ossicles. These bones vibrate against a membrane in the cochlea transmitting the energy to the fluid inside. The fluid moves the organ of Corti stimulating hair cells at the appropriate frequency. The stimulated hair cells then stimulate nerves that send the information to the brain for processing. If hair cells are damaged or lost, then hearing is affected for the frequencies encoded by those sensory cells.

Autoimmune sensorineural hearing loss (AISNHL) in humans has been suspected in systemic autoimmune diseases, and there are indications that inner ear organ-specific autoimmunity is involved in rapidly progressive hearing loss (Harris J P (1993 In: 2nd edition, Otolaryngology Head and Neck Surgery, Vol IV: Ear and Cranial Base (Cummings C W, Krause C J, Schuller D E, Fredrickson J M, Harker L A (eds), Mosby Yearbook, St. Louis, Mo.) pp. 2926-2942; McCabe B F (1979) Ann. Otol. 88:585-859; McCabe B F (1991) In: Bearing Of Basic Research On Clinical Otolaryngology, Adv. Otorhinolaryngol (Pfaltz C R, Arnold W, Kleinsasser O (eds), Karger Publishing, Basel, Switzerland, Vol. 46) pp. 78-81; Hughes et al (1988) Laryngoscope 98:251-253; Harris and Ryan (1984) Am. J. Otolaryngol. 5:418-425; Cruz et al. (1990) Am. J. Otol. 11:342-346; Harris (1983) Otolaryngol Head Neck Surg. 91:17; Arnold et al. (1985) Acta Otolaryngol 99:437; Harris and Sharp (1990) Laryngoscope 100:516-524; Moscicki et al. (1994) JAMA 272:611-616; Sismanis et al. (1997) Otolaryngol Head Neck Surg. 116:146-152). Given the high frequency of idiopathic SNHL, the ability to accurately diagnose autoimmune SNHL (AISNHL) would be of great value since this is one of the few potentially treatable causes of SNHL.

Accordingly, the present invention provides methods of diagnosing the presence of an autoimmune disease in a patient, methods of predicting the response of an autoimmune diseased patient to therapeutic treatment, and methods of monitoring an autoimmune patient's response to therapy. In particular, the present invention relates to a glycoprotein, Inner Ear Supporting Cell Antigen (IESCA) from the inner-ear organ of Corti reactive with a KHRI-3 monoclonal antibody, and methods of using the glycoprotein for predicting the response of autoimmune diseased patients to therapeutic treatment, diagnosing the presence of an autoimmune disease in a patient and for monitoring an autoimmune patient's response to therapy.

Thus, in some embodiments, the present invention provides methods using IESCA antigen and compositions in screening assays for autoimmune disease (e.g., rheumatoid arthritis or AISNHL). The present invention contemplates a variety of methods of testing patients suspected of having an autoimmune disease (e.g., AISNHL), and of those patients who will most likely respond to immunosuppressive therapy (e.g., steroid treatment). The present invention is not limited by the particular method of screening. In some embodiments, guinea pig (or other suitable animal) organ of Corti (or other suitable tissue) is exposed to a patient's sera followed by immunofluorescent staining by methods known to those in the field. In some embodiments, a positive result comprises a distinctive staining pattern of "wine glass" shapes on the organ of Corti (or other distinguishable pattern depending on the tissue used). Staining with MAb KHRI-3, or other suitable antibody, serves as a positive control. The invention is not limited by the tissue used or the animal from which it was derived, so long as when the tissue is stained with antibody that recognizes IESCA, the staining is distinctive. The invention is not limited by the antibody used as a positive control, so long as the antibody is specific for IESCA or an epitope of IESCA.

Another method contemplates providing IESCA (e.g., purified IESCA from source tissue or IESCA produced in vitro as described below) and determining if sera from a patient suspected of having an autoimmune disease (e.g., AISNHL) will react with the antigen. The present invention is not limited by the particular method of screening, or by the particular source of IESCA. One embodiment comprises providing IESCA, and Western blotting IESCA with the patient's sera. Another embodiment comprises making tissue extracts from guinea pig organ of Corti, followed by immunoprecipitation of IESCA with monoclonal antibody KHRI-3, or other suitable antibody, and Western blotting precipitated IESCA with patients' sera. A positive result in either embodiment comprises recognition of IESCA with the patient's sera. Staining with MAb KHRI-3, or other suitable antibody, may serve as a positive control. The invention is not limited by method of generating IESCA (e.g., IESCA can be naturally occurring or obtained via the biological techniques described below), or the animal from which it was derived, so long as IESCA stains with antibody that recognizes IESCA. The invention is not limited by the antibody used as a positive control, so long as the antibody is specific for IESCA or an epitope of IESCA (which can be confirmed in competition assays or preclearing assays with MAb KHRI-3). The presence of antibodies (e.g., auto-antibodies) to IESCA in the serum of patients is associated with autoimmune disease (AISNHL), and, as described below, with the likelihood of responding to therapeutic treatment (e.g., improved hearing).

A. IESCA Polypeptides

In preferred embodiments, the IESCA protein of the present invention is choline transporter-like protein 2 (CTL-2) (See, e.g., Nair et al., Journal of Neuroscience, 24: 1772-1779 (2004); U.S. patent application Ser. No. 09/222,179 filed Dec. 29, 1998, herein incorporated by reference in their entireties for all purposes). In some embodiments, the IESCA protein possesses the same inner ear distribution as CTL-2.

Accordingly, in some embodiments, the present invention provides IESCA polynucleotide sequences (e.g., CTL-2 sequences) that encode IESCA polypeptide sequences. Other embodiments of the present invention provide fragments, fusion proteins or functional equivalents of these IESCA proteins. In some embodiments, the present invention provides truncation mutants of IESCA useful for identifying autoimmune disease or for predicting the response of autoimmune patients to immunosuppressive therapy. In still other embodiment of the present invention, nucleic acid sequences corresponding to IESCA variants, homologs, and mutants may be used to generate recombinant DNA molecules that direct the expression of the IESCA variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, IESCA may be glycosylated or may be non-glycosylated. In other embodiments, the IESCA may also include an initial methionine amino acid residue.

In one embodiment of the present invention, due to the inherent degeneracy of the genetic code, DNA sequences other than the polynucleotide sequences of SEQ ID NO:3 of U.S. patent application Ser. No. 09/222,179, hereby incorporated by reference in its entirety, or homologous sequences thereof (e.g., the human CTL-2 sequence, NCBI Accession Number NM 020428 available at www.ncbi.nlm.nih.gov) that encode substantially the same or a functionally equivalent amino acid sequence, may be used to clone and express IESCA. In general, such polynucleotide sequences hybridize to SEQ ID NO:3, or homologous sequences, under conditions of high to medium stringency as described above. As will be understood by those of skill in the art, it may be advantageous to produce IESCA-encoding nucleotide sequences possessing non-naturally occurring codons. Therefore, in some preferred embodiments, codons preferred by a particular prokaryotic or eukaryotic host (Murray et al., Nucl. Acids Res., 17 (1989)) are selected, for example, to increase the rate of IESCA expression or to produce recombinant RNA transcripts having desirable properties, such as a longer half-life, than transcripts produced from naturally occurring sequence.

1. Vectors for Production of IESCA

IESCA polynucleotides (e.g., CTL2) may be employed for producing polypeptides by recombinant techniques. Thus, for example, IESCA polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising IESCA sequences. In some embodiments of the present invention, the constructs comprise a vector, such as a plasmid or viral vector, into which a IESCA nucleotide sequence has been inserted, in a forward or reverse orientation. In still other embodiments, IESCA sequence is assembled in appropriate phase with translation initiation and termination sequences. In preferred embodiments of the present invention, the IESCA DNA sequence is inserted into the vector using any of a variety of procedures. In general, IESCA DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, IESCA DNA sequence (e.g., CTL2 sequence) in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of IESCA DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of IESCA

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 (1981)), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, (1986)). Alternatively, in some embodiments of the present invention, the IESCA polypeptides of the invention can be synthetically produced by conventional peptide synthesizers.

IESCA proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of IESCA Proteins

The present invention also provides methods for recovering and purifying IESCA from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides IESCA polynucleotides having the IESCA coding sequence fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 (1984)).

4. Fusion Proteins Containing IESCA

The present invention also provides fusion proteins incorporating all or part of IESCA for use in methods of the present invention. Accordingly, in some embodiments of the present invention, the coding sequences for IESCA polypeptide can be incorporated as a part of a fusion gene including a nucleotide sequence encoding a different polypeptide. It is contemplated that this type of expression system will find use under conditions where it is desirable to produce an immunogenic fragment of a IESCA protein. In some embodiments of the present invention, the VP6 capsid protein of rotavirus is used as an immunologic carrier protein for portions of the IESCA polypeptide, either in the monomeric form or in the form of a viral particle. In other embodiments of the present invention, the nucleic acid sequences corresponding to the portion of IESCA against which antibodies are to be raised can be incorporated into a fusion gene construct which includes coding sequences for a late vaccinia virus structural protein to produce a set of recombinant viruses expressing fusion proteins comprising a portion of IESCA as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of IESCA and the poliovirus capsid protein are created to enhance immunogenicity of the set of polypeptide antigens (See e.g., EP Publication No. 025949; and Evans et al., Nature 339:385 (1989); Huang et al., J. Virol., 62:3855 (1988); and Schlienger et al., J. Virol., 66:2 (1992)).

In still other embodiments of the present invention, the multiple antigen peptide system for peptide-based immunization can be utilized. In this system, a desired portion of IESCA is obtained directly from organo-chemical synthesis of the peptide onto an oligomeric branching lysine core (see e.g., Posnett et al., J. Biol. Chem., 263:1719 (1988); and Nardelli et al., J. Immunol., 148:914 (1992)). In other embodiments of the present invention, antigenic determinants of IESCA proteins can also be expressed and presented by bacterial cells.

In addition to utilizing fusion proteins to enhance immunogenicity, it is widely appreciated that fusion proteins can also facilitate the expression of proteins, such as IESCA protein used in the present invention. Accordingly, in some embodiments of the present invention, IESCA can be generated as a glutathione-S-transferase (i.e., GST fusion protein). It is contemplated that such GST fusion proteins will enable easy purification of IESCA, such as by the use of glutathione-derivatized matrices (See e.g., Ausabel et al. (eds.), Current Protocols in Molecular Biology, John Wiley & Sons, NY (1991)). In another embodiment of the present invention, a fusion gene coding for a purification leader sequence, such as a poly-(His)/enterokinase cleavage site sequence at the N-terminus of the desired portion of IESCA, can allow purification of the expressed IESCA fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 (1987); and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of IESCA

Still other embodiments of the present invention provide mutant or variant forms of IESCA (i.e., muteins). In preferred embodiments, the present invention provides mutant or variant forms of CTL2. It is possible to modify the structure of a peptide having an activity of IESCA for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject IESCA proteins as defined herein. A modified peptide can be produced in which the amino acid sequence has been altered, such as by amino acid substitution, deletion, or addition.

Moreover, as described above, variant forms (e.g., mutants or polymorphic sequences) of IESCA proteins are also contemplated as being equivalent to those peptides and DNA molecules that are set forth in more detail. For example, as described above, the present invention encompasses mutant and variant IESCA proteins that contain conservative or nonconservative amino acid substitutions.

This invention further contemplates a method of generating sets of combinatorial mutants of IESCA proteins, as well as truncation mutants, and is especially useful for identifying potential variant sequences (i.e., mutants or polymorphic sequences) that are involved autoimmune disease (e.g., AIS-NHL). The purpose of screening such combinatorial libraries is to generate, for example, novel IESCA variants that can act as either agonists or antagonists, or alternatively, possess novel activities all together.

Therefore, in some embodiments of the present invention, IESCA variants are engineered by the present method to provide altered (e.g., increased or decreased) biological activity. In other embodiments of the present invention, combinatorially-derived variants are generated which have a selective potency relative to a naturally occurring IESCA. Such proteins, when expressed from recombinant DNA constructs, can be used in gene therapy protocols.

Still other embodiments of the present invention provide IESCA variants that have intracellular half-lives dramatically different than the corresponding wild-type protein. For example, the altered protein can be rendered either more stable or less stable to proteolytic degradation or other cellular process that result in destruction of, or otherwise inactivate IESCA. Such variants, and the genes which encode them, can be utilized to alter the location of IESCA expression by modulating the half-life of the protein. For instance, a short half-life can give rise to more transient IESCA biological effects and, when part of an inducible expression system, can allow tighter control of IESCA levels within the cell. As above, such proteins, and particularly their recombinant nucleic acid constructs, can be used in gene therapy protocols.

In still other embodiments of the present invention, IESCA variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of IESCA homologs, variants or other related proteins are aligned, preferably to promote the highest homology possible. Such a population of variants can include, for example, IESCA homologs from one or more species, or IESCA variants from the same species but which differ due to mutation or polymorphisms. Amino acids that appear at each position of the aligned sequences are selected to create a degenerate set of combinatorial sequences.

In a preferred embodiment of the present invention, the combinatorial IESCA library is produced by way of a degenerate library of genes encoding a library of polypeptides which each include at least a portion of potential IESCA protein sequence that find use in the methods of the present invention. For example, a mixture of synthetic oligonucleotides can be enzymatically ligated into gene sequences such that the degenerate set of potential IESCA sequences are expressible as individual polypeptides, or alternatively, as a set of larger fusion proteins (e.g., for phage display) containing the set of IESCA sequences therein.

There are many ways by which the library of potential IESCA homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential IESCA sequences. The synthesis of degenerate oligonucleotides is well known in the art (See e.g., Narang, Tetrahedron Lett., 39:39 (1983); Itakura et al., Recombinant DNA, in Walton (ed.), *Proceedings of the 3rd Cleveland Symposium on Macromolecules*, Elsevier, Amsterdam, pp 273-289 (1981); Itakura et al., Annu. Rev. Biochem., 53:323 (1984); Itakura et al., Science 198:1056 (1984); Ike et al., Nucl. Acid Res., 11:477 (1983)). Such techniques have been employed in the directed evolution of other proteins (See e.g., Scott et al., Science 249:386 (1980); Roberts et al., Proc. Natl. Acad. Sci. USA 89:2429 (1992); Devlin et al., Science 249: 404 (1990); Cwirla et al., Proc. Natl. Acad. Sci. USA 87: 6378 (1990); each of which is herein incorporated by reference; as well as U.S. Pat. Nos. 5,223,409, 5,198,346, and 5,096,815; each of which is incorporated herein by reference).

It is contemplated that IESCA nucleic acids can be utilized as starting nucleic acids for directed evolution. These techniques can be utilized to develop IESCA variants having desirable properties such as increased or decreased ability to function in the methods of the present invention.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 (1996); Leung et al., Technique, 1:11 (1989); Eckert and Kunkel, PCR Methods Appl., 1: 17-24 (1991); Caldwell and Joyce, PCR Methods Appl., 2:28 (1992); and Zhao and Arnold, Nuc. Acids. Res., 25:1307 (1997)). After mutagenesis, the resulting clones are selected for desirable activity (e.g., screened for IESCA activity). Successive rounds of mutagenesis and selection are often necessary to develop enzymes with desirable properties. It should be noted that only the useful mutations are carried over to the next round of mutagenesis.

In other embodiments of the present invention, IESCA polynucleotides of the present invention are used in gene shuffling or sexual PCR procedures (e.g., Smith, Nature, 370: 324 (1994); U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations present in different clones becoming mixed and accumulating in some of the resulting sequences. Multiple cycles of selection and shuffling have led to the functional enhancement of several enzymes (Stemmer, Nature, 370:398 (1994); Stemmer, Proc. Natl. Acad. Sci. USA, 91:10747 (1994); Crameri et al., Nat. Biotech., 14:315 (1996); Zhang et al., Proc. Natl. Acad. Sci. USA, 94:4504 (1997); and Crameri et al., Nat. Biotech., 15:436 (1997)). Variants produced by directed evolution can be screened for IESCA activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of IESCA homologs or variants that find use in the methods of the present invention. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of IESCA

In an alternate embodiment of the invention, the coding sequence of IESCA is synthesized, whole or in part, using chemical methods well known in the art (See e.g., Caruthers et al., Nucl. Acids Res. Symp. Ser., 7:215 (1980); Crea and Horn, Nucl. Acids Res., 9:2331 (1980); Matteucci and Caruthers, Tetrahedron Lett., 21:719 (1980); and Chow and Kempe, Nucl. Acids Res., 9:2807 (1981)). In other embodiments of the present invention, the protein itself is produced using chemical methods to synthesize either an entire IESCA amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. (1983)). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 (1995)) and automated synthesis may be achieved, for example, using ABI 431 A Peptide Synthesizer (Perkin Elmer) in accordance with the instructions provided by the manufacturer. Additionally, the amino acid sequence of IESCA, or any part thereof, may be altered during direct synthesis and/or combined using chemical methods with other sequences to produce a variant polypeptide.

B. IESCA as a Screening Agent for Identifying Autoimmune Disease (e.g., AISNHL) and Predicting Response to Therapy In some embodiments, the present invention provides IESCA protein (e.g., generated by methods described herein) to test for the presence of IESCA antibodies in patient serum, and correlating the presence of antibodies to IESCA in a patient's serum with a higher probability (e.g., compared to a patient without antibodies to IESCA) of the patient responding to immunosuppressive (e.g., corticosteroid) treatment for autoimmune disease (e.g., AISNHL). Therefore, a diagnostic screen based on the detection of anti-IESCA antibodies is provided by the present invention in order to identify patients likely to respond to therapy while sheltering those that do not express anti-IESCA from unnecessary treatment and any unwanted, associated side effects.

In some embodiments, the present invention provides that antibodies to IESCA are detectable by immunofluorescence (IF) in patients with systemic autoimmune disease (e.g., antibodies to IESCA were detected in 8/8 patients studied). Of these, seven had improved hearing following treatment (See, e.g., Table 1). This finding recalls the original observation of McCabe (McCabe BF. (1979) Ann Otol Rhinol Laryngol. 88:585-589) that autoimmune patients with hearing loss often exhibit improved hearing with immunosuppressive therapy. McCabe included patients with systemic autoimmune disease and acknowledged that unilateral disease often progressed to affect both ears but excluded patients with sudden hearing loss developing over periods of less than weeks. Similarly, others (e.g., Moscicki et al. (1994) JAMA 272:611-616) excluded both sudden and unilateral hearing loss from AISNHL, yet many patients who present with unilateral loss progress to the contralateral ear later. Furthermore within the patient populations of the present invention, patients who have developed sudden, sometimes severe, hearing loss in one ear and later progress to worse hearing first in that ear and then later exhibit second episode of sudden hearing loss affecting the opposite ear. Thus, these patients were included in the search for autoantibodies and steroid responsive disease of the present invention since the definitions used by others have somewhat arbitrarily excluded these cases which may represent an earlier and more treatable stage of disease.

In fact, data shows that patients with sudden onset and unilateral progressive hearing loss frequently have antibodies to inner ear antigens. For example, 75% (28/37) of patients with unilateral hearing loss of the present invention were IF positive which is the same proportion found in the bilateral cases (19/26) (73%) (See, e.g., Example 3, Tables 2-3). Additionally, antibodies to IESCA are present in a comparable proportion (5/7) (71%) of sudden (all were unilateral) hearing loss and (42/56) (75%) rapidly progressive hearing loss cases. The probability of hearing improvement was 50-51% in all subgroups.

Since it is widely believed that 30% of patients with idiopathic, unilateral or sudden onset hearing loss are expected to improve spontaneously, the likelihood of improvement being associated with a positive IF test in all subjects as well as in the bilateral group or the unilateral groups was assessed separately. For all subjects the odds ratio for improvement and a positive IF test is 4.92, or stated differently, those patients who improve are nearly 5 times more likely to have antibodies to supporting cells. Accordingly, the present invention provides a method for predicting the response of an autoimmune diseased patient to therapeutic treatment comprising providing an immunipurified glycoprotein from the inner ear organ of Corti reactive with a KHRI-3 monoclonal antibody and serum from a patient suspected of having an autoimmune disease; contacting the glycoprotein with the serum under conditions sufficient to effect binding of the antibody if present to the glycoprotein; detecting binding of an antibody in the serum to the glycoprotein; and correlating the presence or absence of binding to the response of the patient to the therapeutic treatment.

Although statistical significance is lost when the groups are divided into unilateral or bilateral hearing loss, the odds ratios for the association in each group are 4.67 and 5.4 respectively. Furthermore, for the unilateral group the Fishers exact test reached 0.07, indicating a very strong association. The striking similarity of odds ratio between the stratified groups strongly supports the association between IF positivity and hearing improvement in both groups. Finally, for the IF test in the combined groups a 53% improvement rate with 95% confidence intervals of 39-67% were observed indicating that the improvement rate is well above the 1/3 expected by chance alone. Thus, data indicates that many sudden loss patients (7/8 of the tested group) have an autoimmune etiology that includes antibody to IESCA and supporting cells as an important predictive factor of immunosuppressive therapy (e.g., steroid) response.

Although rapidly progressive unilateral and sudden hearing loss (developing over hours or days) has been previously been excluded from AISNHL, laboratory and clinical evidence strongly supports the inclusion of sudden and unilateral hearing loss in AISNHL. In the sudden hearing loss group, 7/8 have antibody to IESCA and supporting cells, and 80% (6/8) improved with steroid treatment. Thus, many sudden onset patients have a steroid responsive autoimmune etiology. Accordingly, in some embodiments, the present invention provides a reliable means of diagnosing autoimmune disease (e.g., AISNHL) through identifying patients possessing sera with antibodies reactive with a IESCA, meaning that physicians no longer need to rely on clinical features and symptoms alone for diagnosing disease in a patient.

Less than 20% of patients with a negative IESCA IF test showed improvement in hearing, whereas more than half of patients with a positive IF test improved. Among the 28 patients with improved hearing after treatment, almost 90% had IESCA antibodies by IF. Accordingly, the present invention provides a method for predicting the response of an autoimmune diseased patient to therapeutic treatment (e.g., steroid treatment). Half of western blot (WB) positive and more than a third of WB negative cases had some degree of recovery. It is not surprising that antibodies to IESCA correlated with treatment outcome better than the WB. WB detects antibodies to 68-72 kDa proteins, of which there could be many in the guinea-pig cochlear tissue. A positive WB result can reflect the presence of antibodies to irrelevant proteins of a similar weight, weakening specificity.

In this regard, heat shock protein 70 also migrates in this region and HSP70 was thought to be the target of autoimmune hearing loss antibodies (Bloch et al., (1995) Arch Otolaryngol Head Neck Surg. 121:1167-1171; Shin et al., (1997) Laryngoscope 107:222-227). A positive western blot for HSP70 was reported to predict steroid response (Hirose et al, (1999) Laryngoscope 109:1749-1754) in AISNHL patients, but many negative patients also responded. More recent studies exclude HSP70 as a specific target of autoantibodies in AISHNL (Billings et al., (1998) Hear Res. 126:210-212; Trune et al., (1998) Hear Res. 116:65-70; Yeom et al., (2003) Laryngoscope. 113:1770-1776). In contrast to the findings for HSP70, the IF test for antibodies to the IESCA identifies a unique binding pattern on supporting cells (Disher et al., (1987) Ann NY Acad Sci., 830:253-265), and a cellular localization already linked to antibody induced hearing loss in an animal model (Nair et al., (1997) Hearing Research, 107:93-101; Nair et al., (1999) Hearing Research 129:50-60). In this study, seven of the 28 patients (25%) who improved with steroid treatment were negative by WB, but six of that seven (86%) were IF positive, thus identifying a group of six responders without detectable antibodies to the 68-72 kDa band. This suggests that the antibody titers were adequate for detection by IF but not for WB. Some western blot negative sera become positive for a 68-72 kDa band when tested on concentrated inner ear antigen precipitated with KHRI-3-coupled beads. This suggests that low titer antibody may be missed on a standard WB assay.

In some embodiments of the present invention, hearing improvement is achieved in patients with inner ear reactive antibodies. In patients with high antibody titer, irreversible damage my have already occurred by the time treatment is started. Some of the patients with rapid onset and profound hearing deficits had very strong staining intensity consistent with high antibody titers. This subset of antibody positive patients may not show improvement. Accordingly, in some embodiments, the present invention provides compositions and methods for the rapid and accurate identification of autoimmune disease (e.g., AISNHL) and, thus, prompt treatment in such cases may prevent additional damage.

For consistency, criteria used in Moscicki et al, supra, was used to define active SNHL and hearing improvement. However, reservations regarding its clinical application and significance exist. A hearing threshold of 30 dB at a single frequency may have limited clinical significance, particularly at 250 or 8000 Hz. In addition, these criteria classify hearing loss patients with a threshold elevation greater 10 dB at just one frequency. It is theoretically possible to have cases where it is impossible for the patient to "recover" based on this criteria, since a greater than 10 dB improvement is required at two consecutive frequencies. Instead of judging loss or improvement at single frequencies, an alternative may be the pure tone average or speech reception threshold to provide a broader picture of the patients' hearing changes, although this would be less sensitive to more modest improvements.

C. Methods of Treating Autoimmune Hearing Loss or Damage and Monitoring the Same 1. Treatment of AISNHL The present invention provides methods of treating AISNHL, where the first step is determining whether a patient experiencing hearing damage or loss has serum antibodies to IESCA. The presence of antibodies indicates a generally favorable response to treatment with steroids or other treatments; thus, patients with anti-IESCA antibodies in their serum are treated accordingly.

Methods of determining whether a patient has AISNHL include mixing a patient's serum sample with purified IESCA, and detecting antibody binding to IESCA by Western blotting, as described in the methods. The source of IESCA includes other animals, such as guinea pig; other sources include recombinant IESCA, produced by well known methods. Other methods for detecting antibody binding to a protein are well known and also useful.

Patients who test positive for the presence of autoantibodies against IESCA are then treated based upon the physician's clinical judgment. Some steroid treatment regimes consist of prednisone at 1 mg per kilogram body weight per day (maximum of 60 mg) for a minimal period of 7 days, followed by a tapering schedule. Patients who demonstrate an initial improvement in hearing that deteriorated as the steroid dosage tapered are maintained on steroids until successful weaning is possible. Other treatment regimes consist of MEDROL dose packs (methylprednisolone 24 mg as a loading dose that can be tapered by 4 milligrams daily for 6 days). Those patients who demonstrate sufficient improvement are not treated further. Patients who do not demonstrate sufficient improvement may receive additional treatment (e.g., with prednisone (e.g., 60 mg per day)). For example, some patients may receive 60 mg/day for seven days followed by a rapid taper, and other patients may receive a 30 day burst at 60 mg/day followed by a slow taper.

2. Gene Therapy Using CTL2

The present invention also provides methods of treating, hearing damage or loss due to mutations present in CTL2 genes. Thus, the invention provides methods and compositions suitable for gene therapy to alter CTL2 expression, production, or function. As described above, the present invention provides CTL2 genes. Thus, the methods described herein are generally applicable. In some embodiments, it is contemplated that the gene therapy is performed by providing a subject with a wild-type allele of CTL2 (i.e., an allele that does not contain a mutation which results in hearing damage or loss). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g. (1992) Miller and Rosman, BioTech., 7:980-990). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. (1991) Mol. Cell. Neurosci., 2:320-330), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 (1992); See also, La Salle et al. (1993) Science 259:988-990); and a defective adeno-associated virus vector (Samulski et al. (1987) J. Virol., 61:3096-3101; Samulski et al. (1989) J. Virol., 63:3822-3828; and Lebkowski et al. (1988) Mol. Cell. Biol., 8:3988-3996).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. The present invention contemplates adenoviruses of both human and animal origin. (See e.g., WO94/26914). Various serotypes of adenovirus exist. Those adenoviruses of animal origin that can be used within the scope of the present invention include adenoviruses of canine, bovine, murine (e.g., Mav1, Beard et al. (1990) Virol., 75-81), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al. (1991) Gene 101:195; EP 185 573; and Graham (1984) EMBO J., 3:2917). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al. (1977) J. Gen. Virol., 36:59), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. Nos. 4,797,368; 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al. (1983) Cell 33:153; Markowitz et al. (1988) J. Virol., 62:1120; PCT/US95/14575; EP 453242; EP178220; Bernstein et al. (1985) Genet. Eng., 7:235; McCormick, (1985) BioTechnol., 3:689; WO 95/07358; and Kuo et al., (1993):845). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al. (1987) Virol., 61:1639). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. (1987) Proc. Natl. Acad. Sci. USA 84:7413-7417; See also, Mackey, et al. (1988) Proc. Natl. Acad. Sci. USA 85:8027-8031; Ulmer et al. (1993) Science 259:1745-1748). The use of cationic lipids may promote encapsulation of negatively charged nucleic acids, and also promote fusion with negatively charged cell membranes (Felgner and Ringold (1989) Science 337:387-388). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931). It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267: 963; Wu and Wu (1988) J. Biol. Chem., 263:14621; and Williams et al. (1991) Proc. Natl. Acad. Sci. USA 88:2726). Receptor-mediated DNA delivery approaches can also be used (Curiel et al. (1992) Hum. Gene Ther., 3:147; and Wu and Wu (1987) J. Biol. Chem., 262:4429).

The present invention also provides a method of monitoring the response of a patient to therapeutic treatment (e.g., immunosuppressive therapy) comprising providing an immunopurified glycoprotein from the inner-ear organ of Corti reactive with a KHRI-3 monoclonal antibody and serum from a patient undergoing therapeutic treatment for autoimmune disease, contacting the glycoprotein with the serum, detecting the presence, absence or degree of binding of an antibody in the serum to the glycoprotein and correlating the amount of binding to the response of the patient to the therapy. In some embodiments, the degree of binding will be lower than the degree of binding observed prior to immunosuppressive therapy. In some embodiments, there will be no change.

In some embodiments, the present invention provides a method of treating a subject with autoimmune disease comprising administering to the subject a composition comprising an agent that binds to autoantibodies (e.g., KHRI-3 antibodies) and removes or neutralizes them. In some embodiments, the agents comprise wild type or modified IESCA proteins or portions thereof. In some embodiments, the agents comprise other proteins or portions thereof or molecules that bind to the autoantibodies. In some embodiments, antibodies (e.g. pooled IgM neutralizing antibodies) are administered that associate with the autoantibodies.

In some embodiments, compositions and methods of the present invention are utilized for research and/or drug screening purposes. For example, in some embodiments, the present invention provides screens or assays to identify compounds that are antagonistic or agonistic for IESCA binding In some embodiments, IESCA (and in particular, fragments of IESCA) are useful in drug screening assays designed to identify drugs that interfere with the specific binding of anti-IESCA to IESCA (e.g., thereby blocking degeneration of the antigen and/or progression of autoimmune sensorineural hearing loss).

In some embodiments, the invention provides isolated IESCA or IESCA polypeptide fragments (e.g., CTL2 polypeptide or fragments thereof). The claimed polypeptide and fragments find particular use in screening assays for agents or lead compounds for agents useful in the diagnosis, prognosis or treatment of disease, particularly disease associated with autoimmune disease (e.g., AISNHL). One such assay involves forming mixtures of 1) IESCA (or fragments thereof) and 2) anti-IESCA (which may or may nor be KHRI-3 MAb), in the presence of 3) a prospective drug candidate. The mixtures are made under conditions that permit the binding of IESCA with anti-IESCA antibody and the mixtures are then analyzed for the presence of such binding. A difference in such binding in the presence of a drug candidate indicates that the agent is capable of modulating the binding of IESCA (or fragments thereof) to anti-IESCA antibody. The assays of the present invention provide for the facile high-throughput screening of compounds suspected to be able to inhibit such binding (e.g., compound libraries, peptide libraries, and the like) to identify potential drug candidates.

In some embodiments, the present invention provides screens to identify compounds that are antagonistic or agonistic for anti-IESCA binding. In another embodiment, anti-IESCA antibodies (or fragments thereof), may be used to screen for compounds that specifically bind to anti-IESCA antibodies and thereby interfere with the binding of anti-IESCA antibodies to IESCA, without binding IESCA. In some embodiments, IESCA (or fragments thereof), can be used to compete against prospective drug candidates in a competition assay. Additionally, it may be used as a positive control.

In some embodiments, the invention utilizes isolated anti-IESCA antibody or anti-IESCA antibody fragments. The antibody and fragments find particular use in screening assays for agents or lead compounds for agents useful in the diagnosis, prognosis or treatment of disease, particularly disease associated with autoimmune disease (e.g., AISNHL). One such assay involves forming mixtures of 1) anti-IESCA antibodies (or fragments thereof) and 2) a prospective drug candidate, and, finally, 3) IESCA (or fragments thereof). The mixtures are made under conditions that permit the binding of the prospective drug candidate with anti-IESCA antibody, followed by the addition of IESCA (or fragments thereof). The mixtures are then analyzed for the presence of such binding of anti-IESCA antibody to IESCA (or fractions thereof). A difference in such binding in the presence of a drug candidate indicates that the agent is capable of modulating the binding of IESCA (or fragments thereof) to anti-IESCA antibody. The assays of the present invention provide for the facile high-throughput screening of compounds suspected to be able to inhibit such binding (e.g., compound libraries, peptide libraries, carbohydrates, and the like) to identify potential drug candidates.

EXPERIMENTAL

The following examples are provided in order to demonstrate and further illustrate certain preferred embodiments and aspects of the present invention and are not to be construed as limiting the scope thereof.

In the experimental disclosure that follows, the following abbreviations apply: N (normal); M (molar); mM (millimolar); .mu.M (micromolar); mol (moles); mmol (millimoles); .mu.mol (micromoles); nmol (nanomoles); pmol (picomoles); g (grams); mg (milligrams); .mu.g (micrograms); ng (nanograms); l or L (liters); ml (milliliters); .mu.l (microliters); cm (centimeters); mm (millimeters); .mu.m (micrometers); nm (nanometers); ° C. (degrees Centigrade); SNHL (Sensorineural Hearing Loss); AISNHL, (Auto Immune Sensorineural Hearing Loss); IESCA (Inner Ear Supporting Cell Antigen); Mab (Monoclonal Antibody); HSP-70 (Heat Shock Protein); IF (Immunofluorescence); SDS PAGE (Sodium dodecyl sulfate polyacrylamide gel electrophoresis).

EXAMPLE 1

Materials and Methods

Patient selection and treatment: Patients with suspected autoimmune inner ear disease were recruited from collaborating otology practices in Pennsylvania, Michigan and Indiana. The University of Michigan Institutional Review Board approved the protocol for the study, and all patients gave written informed consent. A complete medical history, otologic exam, audiologic evaluation with pure-tone and speech audiometry, and tympanometry (American National Standards Institute, standard S3.6, 1986) were obtained. Appropriate imaging and laboratory studies were obtained to exclude other inner ear disorders. Informed consent and control sera were obtained from 20 normal volunteers ranging in age from 20 to 52 who have no hearing-related complaints. Sera were analyzed for a 68-72 kDa band on WB of guinea pig inner ear extract and for antibodies to IESCA using IF on guinea pig organ of Corti surface preparations.

This analysis includes 63 patients who met the inclusion criteria of active, rapidly progressive, unilateral or bilateral sensorineural hearing loss documented by a pretreatment audiogram, treatment with a standard course of steroids, and post treatment audiologic assessment within 6 weeks of initial presentation. Active hearing loss was defined as a pure tone threshold of 30 dB HL or greater at any single frequency with evidence of 10 dB or greater deterioration in any frequency within 3 months prior to the serum draw. Hearing improvement was defined as a greater than 10 dB threshold improvement at two consecutive frequencies and/or a 20% increase in speech discrimination score as previously defined (See, e.g., Moscicki, et al., JAMA. 272:611-616 (1994)).

All patients were treated based on the clinical judgment of their physician without knowledge of the antibody assay results. The majority of patients (52/63)(83%), received prednisone 1 mg per kilogram body weight per day (maximum of 60 mg) for a minimal period of 7 days, followed by a tapering schedule. Patients who had an initial improvement in hearing that deteriorated as the steroid dosage tapered were maintained on steroids until successful weaning was possible. Eleven patients (17%) received Medrol® dose packs (methylprednisolone 24 mg as a loading dose that was tapered by 4 milligrams daily for 6 days). Nine of these patients showed a considerable improvement and no further treatment was given. The other two (patients 10 and 18) received additional treatment. One (pt 18) received 60 mg/day for seven days followed by a rapid taper, and patient 10 had a 30 day burst at 60 mg/day followed by a slow taper. Both improved following this more intense therapy.

Western Blot Analysis: The University of Michigan Committee on Use and Care of Animals approved all studies and the Unit for Laboratory Animal Medicine provided Veterinary care and housing. Guinea pigs (250-300 g) were anesthetized and decapitated. Tissue extracts were prepared as described (See, e.g., Disher et al., Ann NY Acad Sci. 830:253-65 (1987)). The organ of Corti, including the modiolus but without the spiral ligament, together with vestibular tissues from the ampulla, sacule, and utricle were harvested and solubilized on ice in lysis buffer (1% NP-40 in PBS pH 7.2) containing protease inhibitors (1 mM PMSF, leupeptin 1 µg/mL, antipain 2 µg/mL, benzamidine 10 µl/mL, aprotinin 10 ku/mL, chymostatin 1 µg/mL, pepstatin 1 µg/mL), homogenized and allowed to stand at 4° C. for 30 minutes. After low speed centrifugation (1000 rpm for 3 min) to remove bone, the lysate was mixed 1:3 with 4x sample buffer to give these final concentrations, 0.0625 M tris-HCL pH 6.8, 2% SDS, 10% glycerol, 5% 2-mercaptoethanol and 0.005% bromophenol blue. The samples were boiled for 2 minutes, loaded into a 3"×5" 7% polyacrylamide gel and electrophoresed for 2 hours at 100 V/gel. Electrophoretic transfer to a nitrocellulose membrane was carried out at 25 V/gel overnight. The membranes were cut into strips, soaked in 5% milk in PBS-0.1% Tween to block nonspecific binding, and incubated for 2 hours at room temperature with human serum diluted 1:50 in the 5% milk solution. The strips were washed 3 times for 10 minutes each, and incubated for 2 hours at room temperature with secondary antibody (goat anti-human IgG/IgM conjugated with horseradish peroxidase (Jackson ImmunoResearch Laboratories, Inc., West Grove, Pa.), diluted to 1:500. The blots were washed three times and developed in 4-chloro-1-napthol (0.5 mg/mL) in methanol-PBS, pH 7.6 (1:5) containing 0.05% hydrogen peroxide for 1.5-2 minutes. Colored molecular-weight markers (Amersham, Arlington Heights, Ill.) were used to construct a semi-log plot of relative molecular mass versus electrophoretic migration distance for each gel. Sera were scored for staining of a protein migrating at 68-72 kDa.

Immunofluorescence

Guinea pig inner ear was fixed in freshly prepared 2% paraformaldehyde for 2 hours, dissected free of bone, the spiral ligament and the tectorial membrane, then the modiolus and the organ of Corti were halved, incubated in 3% goat serum in PBS for 1 hour, washed, and each half was incubated overnight at 4° C. in patient or control serum diluted 1:50 in PBS. The specimens were washed, incubated for 45 minutes at 23° C. with rhodamine conjugated anti-human goat IgG/IgM heavy and light chain-specific antibody (Jackson ImmunoResearch Laboratories, Inc., West Grove, Pa.), diluted 1:200 in PBS (pH 7.4). After 3 washes the organ of Corti was dissected free of the modiolus, mounted in GVA mounting media (Zymed Labs, San Francisco, Calif.), and examined by confocal microscopy. A "wine glass"-staining staining pattern (Zajic et al., Hear Res. 52(1):59-71 (1991); Nair et al., Hear Res. 83(1-2):101-13 (1995); Nair et al., Hear Res. 107 (1-2):93-101 (1997); Disher et al., *Ann NY Acad Sci*. 830:253-65 (1987)) was considered positive for antibodies to IESCA.

Statistical analysis: Given the dichotomous nature of the study measures and outcomes, data were analyzed using the Chi square test and the Fisher exact test as appropriate. A two-sided alpha level of less than 0.05 was considered statistically significant.

EXAMPLE 2

Patients Evaluated for Antibody to Inner Ear Antigens and for Response to Steroid Treatment Sixty-three of 159 patients met the inclusion criteria for active, unilateral or bilateral sensorineural hearing loss, with no other etiology for hearing loss. Each had serum drawn immediately prior to the onset of steroid therapy, and had appropriate audiological follow-up. There were 33 males and 30 females (Table 1) with a mean age of 47 years (range=4.1-84 years; SD=17.8). Eight (13%) had a history of one or more systemic autoimmune diseases which included Cogan's syndrome, systemic lupus erythematosus, unclassified autoimmunity, Raynaud's phenomenon, Hashimoto's thyroiditis, rheumatoid arthritis, and Wegener's granulomatosis (Table 1).

TABLE 1

Patients evaluated for antibody to inner ear antigens and for response to steroid treatment.

| UMHL Patient No. | Age | Gender/other autoimmune | WB Result | IF Result | Pre-Treatment PTA (r/l) | Post-Treatment PTA (r/l) | Improvement | Type of Hearing loss | Sidedness |
|---|---|---|---|---|---|---|---|---|---|
| 4 | 39 | Male/Cogans[1] | Positive | Positive | 107/102[2] | 116/110 | − | Rapidly Progressive | Left |
| 5 | 63 | Male/SLE | Positive | Positive | 00/57 | 81/31 | + | Rapidly Progressive | Left |
| 6 | 75 | Male | Positive | Positive | 00/70 | 81/30 | + | Rapidly Progressive | Left |
| 8 | 27 | Female/uncl | Negative | Positive | 20/61 | 26/40 | + | Sudden | Left |
| 9 | 33 | Female | Positive | Positive | 1.3/57 | 10/5 | + | Sudden | Left |
| 10 | 44 | Female | Positive | Positive | 48/61 | 28/62 | + | Rapidly Progressive | Bilateral |
| 11 | 47 | Male | Negative | Positive | 00/32 | 00/33 | − | Rapidly Progressive | Left |
| 17 | 53 | Female | Positive | Positive | 52/98 | 45/00 | − | Rapidly Progressive | Right |
| 18 | 49 | Male | Positive | Positive | 35/71 | 33/73 | − | Rapidly Progressive | Bilateral |
| 19 | 22 | Male | Positive | Positive | 22/40 | 28/38 | − | Rapidly Progressive | Bilateral |
| 20 | 51 | Female | Positive | Positive | 81/45 | 81/21 | + | Rapidly Progressive | Left |
| 21 | 38 | Male | Positive | Positive | 47/42 | 37/42 | + | Rapidly Progressive | Left |
| 22 | 39 | Male | Negative | Negative | 25/00 | 20/00 | − | Rapidly Progressive | Left |
| 23 | 65 | Female | Negative | Negative | 25/28 | 25/22 | − | Rapidly Progressive | Bilateral |
| 24 | 55 | Male | Negative | Positive | 62/58 | 42/56 | + | Rapidly Progressive | Bilateral |
| 27 | 62 | Female | Positive | Positive | 46/3.8 | 47/8.8 | − | Rapidly Progressive | Right |
| 28 | 62 | Female/Raynaud's | Negative | Positive | 122/5 | 92/6.3 | + | Sudden | Right |
| 29 | 84 | Female/RA | Positive | Positive | 33/70 | 33/77 | − | Rapidly Progressive | Left |
| 31 | 14 | Male | Negative | Negative | 00/77 | 97/98 | − | Rapidly Progressive | Left |
| 32 | 43 | Male | Positive | Negative | 76/10 | 27/6.3 | + | Sudden | Right |
| 33 | 48 | Male | Positive | Positive | 53/45 | 46/35 | + | Rapidly Progressive | Bilateral |
| 35 | 63 | Male | Negative | Positive | 62/20 | 58/20 | − | Rapidly Progressive | Left |
| 36 | 16 | Female | Negative | Negative | 7.5/00 | 7.5/00 | − | Sudden | Left |
| 37 | 65 | Female | Positive | Positive | 25/52 | 21/25 | + | Sudden | Left |
| 39 | 70 | Male | Positive | Positive | 75/20 | 72/5 | + | Rapidly Progressive | Left |
| 42 | 79 | Male | Negative | Negative | 45/50 | 52/50 | − | Rapidly Progressive | Left |
| 43 | 60 | Female | Negative | Positive | 53/00 | 43/00 | + | Rapidly Progressive | Right |

TABLE 1-continued

Patients evaluated for antibody to inner ear antigens and for response to steroid treatment.

| UMHL Patient No. | Age | Gender/other autoimmune | WB Result | IF Result | Pre-Treatment PTA (r/l) | Post-Treatment PTA (r/l) | Improvement | Type of Hearing loss | Sidedness |
|---|---|---|---|---|---|---|---|---|---|
| 48 | 37 | Female | Positive | Negative | 50/33 | 46/35 | − | Rapidly Progressive | Bilateral |
| 49 | 66 | Female | Positive | Positive | 00/55 | 00/25 | + | Rapidly Progressive | Left |
| 51 | 66 | Male | Positive | Positive | 25/82 | 23/72 | + | Rapidly Progressive | Left |
| 52 | 35 | Male | Negative | Positive | 36/33 | 26/32 | + | Rapidly Progressive | Bilateral |
| 54 | 58 | Male | Negative | Negative | 60/70 | 35/50 | + | Rapidly Progressive | Bilateral |
| 55 | 62 | Male | Positive | Positive | 38/100 | 36/60 | + | Rapidly Progressive | Left |
| 56 | 54 | Male | Positive | Positive | 33/47 | 27/38 | − | Rapidly Progressive | Bilateral |
| 58 | 29 | Male | Positive | Positive | 13/10 | 10/8 | − | Sudden | Right |
| 61 | 30 | Female | Negative | Negative | 42/26 | 48/40 | − | Rapidly Progressive | Bilateral |
| 72 | 55 | Female | Positive | Positive | 10/12 | 10/27 | − | Rapidly Progressive | Bilateral |
| 74 | 39 | Female | Negative | Negative | 65/57 | 62/57 | − | Rapidly Progressive | Bilateral |
| 77 | 69 | Female | Negative | Negative | 26/63 | 25/58 | − | Rapidly Progressive | Bilateral |
| 79 | 58 | Male | Positive | Positive | 13/38 | 30/41 | − | Rapidly Progressive | Bilateral |
| 80 | 34 | Male | Positive | Positive | 71/32 | 77/42 | − | Rapidly Progressive | Bilateral |
| 81 | 40 | Female | Positive | Positive | 25/13 | 18/1.3 | + | Rapidly Progressive | Bilateral |
| 82 | 33 | Female | Negative | Positive | 3.8/82 | 7.5/55 | + | Sudden | Left |
| 83 | 37 | Female/SLE, RA | Positive | Positive | 30/35 | 30/25 | + | Rapidly Progressive | Right |
| 86 | 72 | Female | Positive | Negative | 72/68 | 68/65 | − | Rapidly Progressive | Left |
| 87 | 33 | Female | Positive | Positive | 20/3 | 13/5 | − | Rapidly Progressive | Right |
| 90 |  | Male | Positive | Negative | 57/32 | 56/31 | − | Rapidly Progressive | Right |
| 92 | 46 | Female | Negative | Positive | 55/56 | 55/60 | − | Rapidly Progressive | Left |
| 96 | 4 | Male | Negative | Positive | 92/61 | 90/61 | − | Rapidly Progressive | Bilateral |
| 101 | 44 | Male | Negative | Negative | 31/33 | 30/31 | − | Rapidly Progressive | Left |
| 106 | 43 | Female | Positive | Positive | 17/25 | 17/21 | − | Rapidly Progressive | Left |
| 110 | 70 | Male/Wegener's | Positive | Positive | 102/28 | 91/26 | + | Rapidly Progressive | Bilateral |
| 116 | 58 | Male | Positive | Positive | 00/28 | 00/55 | − | Rapidly Progressive | Left |
| 118 | 25 | Female | Positive | Positive | 43/11 | 11/7.5 | + | Rapidly Progressive | Right |
| 132 | 50 | Male | Positive | Negative | 57/18 | 46/18 | + | Rapidly Progressive | Right |
| 142 |  | Female | Positive | Positive | 61/58 | 55/50 | − | Rapidly Progressive | Bilateral |
| 146 | 46 | Male | Positive | Positive | 90/57 | 78/62 | + | Rapidly Progressive | Bilateral |
| 149 | 46 | Male | Positive | Positive | 82/56 | 80/60 | − | Rapidly Progressive | Bilateral |
| 151 | 22 | Male | Positive | Positive | 45/55 | 43/51 | − | Rapidly Progressive | Bilateral |
| 152 | 6 | Female | Positive | Positive | 55/25 | 55/18 | − | Rapidly Progressive | Right |
| 153 | 34 | Female/Thyroiditis | Positive | Positive | 35/21 | 24/13 | + | Rapidly Progressive | Bilateral |
| 157 | 43 | Female | Positive | Positive | 45/40 | 35/31 | + | Rapidly Progressive | Bilateral |
| 159 | 54 | Male | Positive | Negative | 73/61 | 73/62 | − | Rapidly Progressive | Bilateral |

Footnotes
[1]Other autoimmune diseases are indicated for individual patients. Cogan's = Cogan's syndrome; SLE = systemic lupus erythematosus; uncl = unclassified systemic autoimmune disease; Raynaud's = Raynaud's syndrome; RA = rheumatoid arthritis; Wegener's = Wegener's granulomatosis; Thyroiditis = Hashimoto's thyroiditis. Patient 5 has lupus and temporal arteritis. Patient 83 has both lupus and RA. Patient 153 has Hashimoto's thyroiditis, rheumatoid arthritis, Raynaud's syndrome and lupus.
[2]PTA = pure tone average of 0.5, 1, 2, 4 kHz, given for left (l)/right (r) ears respectively. 00 = no response to sound The left ear was affected in 26 patients, the right in 12, and 25 had hearing loss in both ears Table 1). Although hearing loss was the primary otologic symptom, 83% (52/63) also complained of tinnitus, 57% (36/63) had aural fullness and 36 had vestibular symptoms. Eight (13%) had rapid onset hearing loss with progression over hours or days.

In the study sample, the mean of the four frequency (0.5, 1, 2, 4 kHz) pure tone average (PTA) of all ears with active hearing loss was 52.7 dB (SD=25.5 dB) and the mean speech discrimination score was 69.4% (SD=29.9%). Following treatment, the four frequency average for all active hearing loss ears had a mean of 43.7 dB (SD=23.5 dB) and the speech discrimination mean was 78.1% (SD=28%).

Of the 63 patients, sera from 43 (68%) were western blot positive and sera from 47 (75%) were IF positive. Sera from 37 patients (59%) were positive in both assays, 10 were negative in both and 16 were discordant (positive in one and negative in the other) (Table 1).

Patient sera from UMHL-6, -9, -33 exhibit the typical "wineglass" staining pattern of the outer pillar cell phalangeal processes that is reminiscent of the KHRI-3 monoclonal antibody staining (Disher et al., Ann NY Acad Sci. 830:253-65 (1987)). These sera also stain a protein band migrating in the 68-72 kDa region and all three patients responded to therapy (Table 1). Sera with concordant and discordant results in the two assays are shown (FIG. 1). Results are shown for patient UMHL-80 who had rapidly progressive bilateral hearing loss and failed to respond to treatment (FIG. 1, lane A and Table 1). This patient had very strong staining in both assays, which is consistent with a high level of circulating antibody. Results with sera from patient UMHL-82, who had unilateral sudden onset hearing loss, are also shown (Table 1). Her serum contains antibody to supporting cells, but little or no detectable antibody to the 68-72 kDa protein bands. She responded favorably to treatment (Table 1). Panel C and Lane C show results from Patient UMHL-48, who had rapidly progressive bilateral hearing loss but did not respond to treatment. Her serum did not stain supporting cells but did stain a 68-72 kDa band on WB. This patient's serum contains antibody to stereocilia. Stereocilia antibodies are often present in normal mouse and human sera, as well as in patient's sera, but its significance is unknown. Patient UMHL-54 had rapidly progressive bilateral hearing loss and responded to treatment (Table 1) but had no detectable antibody by either assay (Panel D and Lane D). None of the 20 normal sera stained supporting cells and only one stained a 68-72 kDa protein in WB.

EXAMPLE 3

Western Blot and Immunofluorescence Results in Relation to Hearing Improvement after Steroid Treatment Hearing improvement was documented in 49% (21/43) of patients who were western blot positive and 35% (7/20) of WB negative patients (p=0.304) (Table 2). Of those who improved 89% (25/28) were positive for antibody to supporting cells by the IF assay and only 10.7% (3/28) were IF negative. Of the 47 patients who were IF positive, 53% (25/47) had hearing improvement. In contrast only 19% (3/16) of those who were IF negative improved (Relative Rate: 2.8) (p=0.017) (Table 3). Patients whose acute phase sera are IF positive are nearly three times more likely to experience improved hearing with steroid treatment than patients whose sera are IF negative. Thus antibody to supporting cells is significantly associated with hearing improvement following steroid treatment. When both tests were combined, 51% (19/37) of those who were positive by both assays showed improvement, compared with 10% (1/10) who were negative by both tests. The combined results of both tests also were significantly associated with response to therapy (p=0.03).

TABLE 2

WB results in relation to hearing improvement after steroid treatment.

|  | Improvement in hearing | No improvement in hearing | Total |
| --- | --- | --- | --- |
| WB positive | 21 (49%) | 22 (51%) | 43 (100%) |
| WB negative | 7 (35%) | 13 (65%) | 20 (100%) |
| Total | 28 (44%) | 35 (56%) | 63 (100%) | p = 0.303

TABLE 3

IF results in relation to hearing improvement after steroid treatment

|  | Improvement in hearing | No improvement in hearing | Total |
| --- | --- | --- | --- |
| IF positive | 25 (53%) | 22 (47%) | 47 (100%) |
| IF negative | 3 (19%) | 13 (81%) | 16 (100%) |
| Total | 28 (44%) | 35 (56%) | 63 (100%) | p = 0.017

All eight patients with systemic autoimmune disease (Table 1) had antibody to inner ear antigens; six (75%) by WB and eight (100%) by IF. Of these eight patients, six (75%) demonstrated hearing improvement following treatment.

Forty-nine patients were tested for ESR, RF, and ANA; of these 32 (65%) were within normal limits and 17 (35%) were not. Of the 17 with abnormal tests, 11 (65%) had improved hearing and 6 (35%) did not; this was not significantly different from the group with normal values for ESR, RF, and ANA, of which 17 (53%) of 32 improved and 15 (47%) did not (p=0.43). There was no association of antibody to inner ear antigens by age group, gender or ABO blood type.

A somewhat higher proportion of patients with unilateral hearing loss 18/37 (48.6%) showed improvement after steroids compared to 10/26 (38.4%) of those with bilateral hearing loss. This observation is consistent with the earlier stage of disease in unilateral patients who have not yet progressed to involvement of both ears and thus may have acquired less damage to the inner ear. It is of interest that of the 8 patients with rapid onset hearing loss (marked as sudden in Table 1), all but one has antibody to inner ear antigens, detected either as the 68-72 kDa band on western blots (4/8) or to supporting cells (6/8) or both. One of these patients (UMHL28, Table 1) also has Raynaud's syndrome, a systemic autoimmune disease. Six of the eight with very rapid onset hearing loss improved after steroid treatment. Of these, five have antibody to supporting cells and 3 have antibody to the 68-72 kDa band on WB. There was no improvement in the single sudden onset patient without antibody.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method for predicting the response of a subject with autoimmune sensorineural hearing loss to immunosuppressive steroid therapy, comprising:
    a. providing:
        i), synthetic or recombinant CTL2 protein reactive with a KHRI-3 monoclonal antibody; and
        ii) serum from a subject with autoimmune sensorineural hearing loss;
    b. contacting said synthetic or recombinant CTL2 protein with said serum under conditions sufficient to effect binding of CTL2-specific antibodies, if present in said serum, to said CTL2 protein;
    c. identifying the presence of said CTL2-specific antibodies in said serum by detecting binding of said antibodies to said CTL2 protein; and
    d. correlating the presence or absence of said binding to the likelihood of said subject to respond to immunosuppressive steroid therapy wherein detection of binding of said antibodies to said CTL2 protein is indicative of a subject more likely to respond to immunosuppressive therapy compared to a subject from whom binding of said antibodies to said CTL2 protein is not detected.

2. The method of claim 1, wherein said patient is experiencing autoimmune disease selected from the group consisting of rheumatoid arthritis, multiple sclerosis, juvenile-onset diabetes, systemic lupus erythematosus, Cogan's syndrome, unclassified systemic autoimmune disease, Raynaud's syndrome, Wegener's granulomatosis, autoimmune uveoretinitis, autoimmune vasculitis, bullous pemphigus, myasthenia gravis, autoimmune thyroiditis, Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura.

3. The method of claim 1, wherein immunofluorescence is used for said detecting.

4. The method of claim 1, wherein said detecting comprises Western blotting.

5. The method of claim 1, wherein said subject with autoimmune sensorineural hearing loss has unilateral autoimmune sensorineural hearing loss.

6. The method of claim 1, wherein said subject with autoimmune sensorineural hearing loss has bilateral autoimmune sensorineural hearing loss.

* * * * *